(12) United States Patent
Adiri et al.

(10) Patent No.: US 11,026,624 B2
(45) Date of Patent: Jun. 8, 2021

(54) MEASURING AND MONITORING SKIN FEATURE COLORS, FORM AND SIZE

(71) Applicant: HEALTHY.IO LTD., Tel Aviv (IL)

(72) Inventors: Yonatan Adiri, Tel Aviv (IL); Ido Omer, Ramat Hasharon (IL); Shachar Mendelowitz, Tel Aviv (IL); Roee Salomon, Herzliya (IL)

(73) Assignee: HEALTHY.IO LTD., Tel Aviv (IL)

( * ) Notice: Subject to any disclaimer, the term of this patent is extended or adjusted under 35 U.S.C. 154(b) by 99 days.

(21) Appl. No.: 16/438,649

(22) Filed: Jun. 12, 2019

(65) Prior Publication Data

US 2019/0290187 A1    Sep. 26, 2019

Related U.S. Application Data

(63) Continuation of application No. 15/546,674, filed as application No. PCT/IL2016/050069 on Jan. 21, 2016, now Pat. No. 10,362,984.
(Continued)

(51) Int. Cl.
*A61B 5/00* (2006.01)
*H04N 1/62* (2006.01)
(Continued)

(52) U.S. Cl.
CPC ............ *A61B 5/444* (2013.01); *A61B 5/0077* (2013.01); *A61B 5/1032* (2013.01);
(Continued)

(58) Field of Classification Search
CPC ....... G06T 7/90; G06T 7/0016; G06K 9/6298; H04N 1/628
See application file for complete search history.

(56) References Cited

U.S. PATENT DOCUMENTS

| 5,852,675 A | 12/1998 | Matsuo et al. |
| 7,162,063 B1 | 1/2007 | Craine et al. |

(Continued)

FOREIGN PATENT DOCUMENTS

| WO | WO 2008/036343 | 3/2008 |
| WO | WO 2013066642 | 5/2013 |

(Continued)

OTHER PUBLICATIONS

Maglogiannes et al; A system for the acquisition of reproducible digital skin lesions images; Technology and Health Care; IOS Press; vol. 11; Publication online Feb. 2003; retrieved May 11, 2016.
(Continued)

*Primary Examiner* — Edward Park
(74) *Attorney, Agent, or Firm* — Finnegan, Henderson, Farabow, Garrett & Dunner LLP

(57) ABSTRACT

Kits, diagnostic systems and methods are provided, which measure the distribution of colors of skin features by comparison to calibrated colors which are co-imaged with the skin feature. The colors on the calibration template (calibrator) are selected to represent the expected range of feature colors under various illumination and capturing conditions. The calibrator may also comprise features with different forms and size for calibrating geometric parameters of the skin features in the captured images. Measurements may be enhanced by monitoring over time changes in the distribution of colors, by measuring two and three dimensional geometrical parameters of the skin feature and by associating the data with medical diagnostic parameters. Thus, simple means for skin diagnosis and monitoring are provided which simplify and improve current dermatologic diagnostic procedures.

19 Claims, 8 Drawing Sheets

Related U.S. Application Data

(60) Provisional application No. 62/108,097, filed on Jan. 27, 2015.

(51) Int. Cl.
    *A61B 5/107* (2006.01)
    *A61B 5/103* (2006.01)
    *G06T 7/90* (2017.01)
    *G06K 9/62* (2006.01)
    *G06T 7/00* (2017.01)

(52) U.S. Cl.
CPC .......... *A61B 5/1034* (2013.01); *A61B 5/1077* (2013.01); *A61B 5/1079* (2013.01); *G06K 9/6298* (2013.01); *G06T 7/0016* (2013.01); *G06T 7/90* (2017.01); *H04N 1/628* (2013.01); A61B 5/7264 (2013.01); A61B 5/743 (2013.01); A61B 2560/0233 (2013.01); A61B 2576/02 (2013.01); G06T 2207/30088 (2013.01); G06T 2207/30096 (2013.01)

(56) References Cited

U.S. PATENT DOCUMENTS

| | | |
|---|---|---|
| D720,864 S | 1/2015 | Behar et al. |
| D735,879 S | 8/2015 | Behar et al. |
| 9,285,323 B2 | 3/2016 | Burg et al. |
| 9,311,520 B2 | 4/2016 | Burg et al. |
| D758,608 S | 6/2016 | Behar et al. |
| 9,528,941 B2 | 12/2016 | Burg et al. |
| 9,607,380 B2 | 3/2017 | Burg et al. |
| D783,838 S | 4/2017 | Zhao et al. |
| 9,690,904 B1 | 6/2017 | Zizi |
| 9,808,206 B1 | 11/2017 | Zhao et al. |
| 9,818,193 B2 | 11/2017 | Smart |
| 9,863,811 B2 | 1/2018 | Burg |
| D831,197 S | 10/2018 | Scruggs et al. |
| 10,143,425 B1 | 12/2018 | Zhao et al. |
| 10,267,743 B2 | 4/2019 | Burg et al. |
| 2002/0016539 A1* | 2/2002 | Michaelis ............... A61B 5/411 600/407 |
| 2006/0153430 A1* | 7/2006 | Canzler ............... G06K 9/00281 382/118 |
| 2008/0304736 A1* | 12/2008 | Nakagawa ................ G06T 7/90 382/165 |
| 2011/0216204 A1* | 9/2011 | Elwell .................... H04N 17/02 348/184 |
| 2011/0273535 A1* | 11/2011 | Mendelson ............ A61B 5/444 348/43 |
| 2011/0286003 A1* | 11/2011 | Ono ....................... G01B 11/22 356/495 |
| 2014/0148708 A1 | 5/2014 | Cosentino et al. |
| 2014/0257058 A1 | 9/2014 | Clarysse et al. |
| 2015/0044098 A1 | 2/2015 | Smart et al. |
| 2015/0313484 A1 | 11/2015 | Burg et al. |
| 2016/0095567 A1* | 4/2016 | Tachikawa ............. A61B 6/542 378/98.2 |
| 2016/0163028 A1 | 6/2016 | Xu et al. |
| 2017/0098137 A1 | 4/2017 | Burg et al. |
| 2017/0258340 A1 | 9/2017 | Przybyszewski et al. |
| 2018/0252585 A1 | 9/2018 | Burg |
| 2019/0290187 A1* | 9/2019 | Ariri .................... H04N 1/6033 |
| 2019/0298183 A1 | 10/2019 | Burg et al. |
| 2019/0307337 A1 | 10/2019 | Little et al. |
| 2019/0307400 A1 | 10/2019 | Zhao et al. |
| 2019/0310203 A1 | 10/2019 | Burg et al. |
| 2019/0350535 A1 | 11/2019 | Zhao et al. |
| 2020/0196962 A1 | 6/2020 | Zhao et al. |
| 2020/0225166 A1 | 7/2020 | Burg et al. |
| 2020/0286600 A1 | 9/2020 | DeBrouwer et al. |

FOREIGN PATENT DOCUMENTS

| | | |
|---|---|---|
| WO | WO 2013/093851 | 6/2013 |
| WO | WO 2013116253 | 8/2013 |
| WO | WO 2013116316 | 8/2013 |
| WO | WO 2014025415 | 2/2014 |
| WO | WO 2015134820 | 9/2015 |
| WO | WO 2015171667 | 11/2015 |
| WO | WO 2016025935 | 2/2016 |
| WO | WO 2017127778 | 7/2017 |
| WO | WO 2017156501 | 9/2017 |

OTHER PUBLICATIONS

U.S. Appl. No. 14/283,208.
U.S. Appl. No. 14/283,210.
U.S. Appl. No. 14/283,211.
U.S. Appl. No. 14/283,213.
U.S. Appl. No. 14/641,303.
U.S. Appl. No. 16/215,623.
U.S. Appl. No. 15/812,452.
U.S. Appl. No. 15/390,714.
U.S. Appl. No. 14/675,719.
Design U.S. Appl. No. 29/491,524.

* cited by examiner

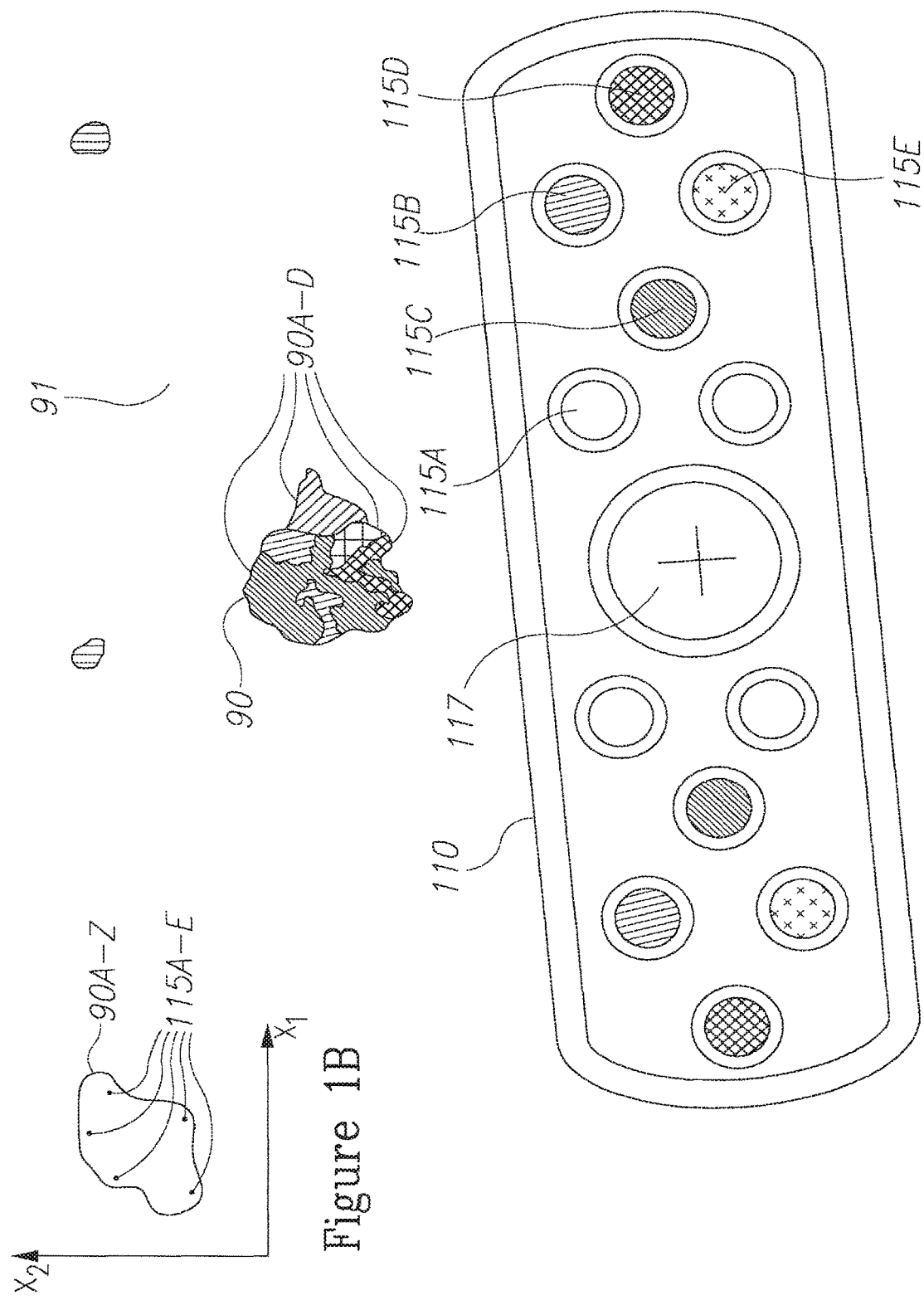

*200*

- 210 — SELECTING COLORS, FORMS AND/OR SIZES ACCORDING TO EXPECTED COLORS, FORMS AND/OR SIZES IN A SKIN FEATURE, A SPECIFIED SET OF ILLUMINATION CONDITIONS AND A SPECIFIED SET OF CAPTURING PARAMETERS
- 212 — OPTIMIZING THE COLOR, FORM AND/OR SIZE SELECTION WITH RESPECT TO VARYING ILLUMINATION AND CAPTURING CONDITIONS
- 215 — SELECTING THE COLORS TO SPAN A COLOR SPACE DEFINED BY A MEDICAL APPLICATION
- 220 — PREPARING A COLOR TEMPLATE HAVING THE SELECTED COLORS TO BE ATTACHABLE ONTO A SKIN AREA NEXT TO A SKIN FEATURE
- 225 — ATTACHING A CALIBRATOR COMPRISING A PLURALITY OF COLOR AREAS AND/OR AREAS OF DIFFERENT FORM(S) AND SIZE(S) ONTO A SKIN AREA NEXT TO A SKIN FEATURE
- 230 — CAPTURING IMAGE(S) OF THE SKIN FEATURE AND THE CALIBRATOR
- 232 — CAPTURING MULTIPLE IMAGES OF THE SKIN FEATURE

Figure 3

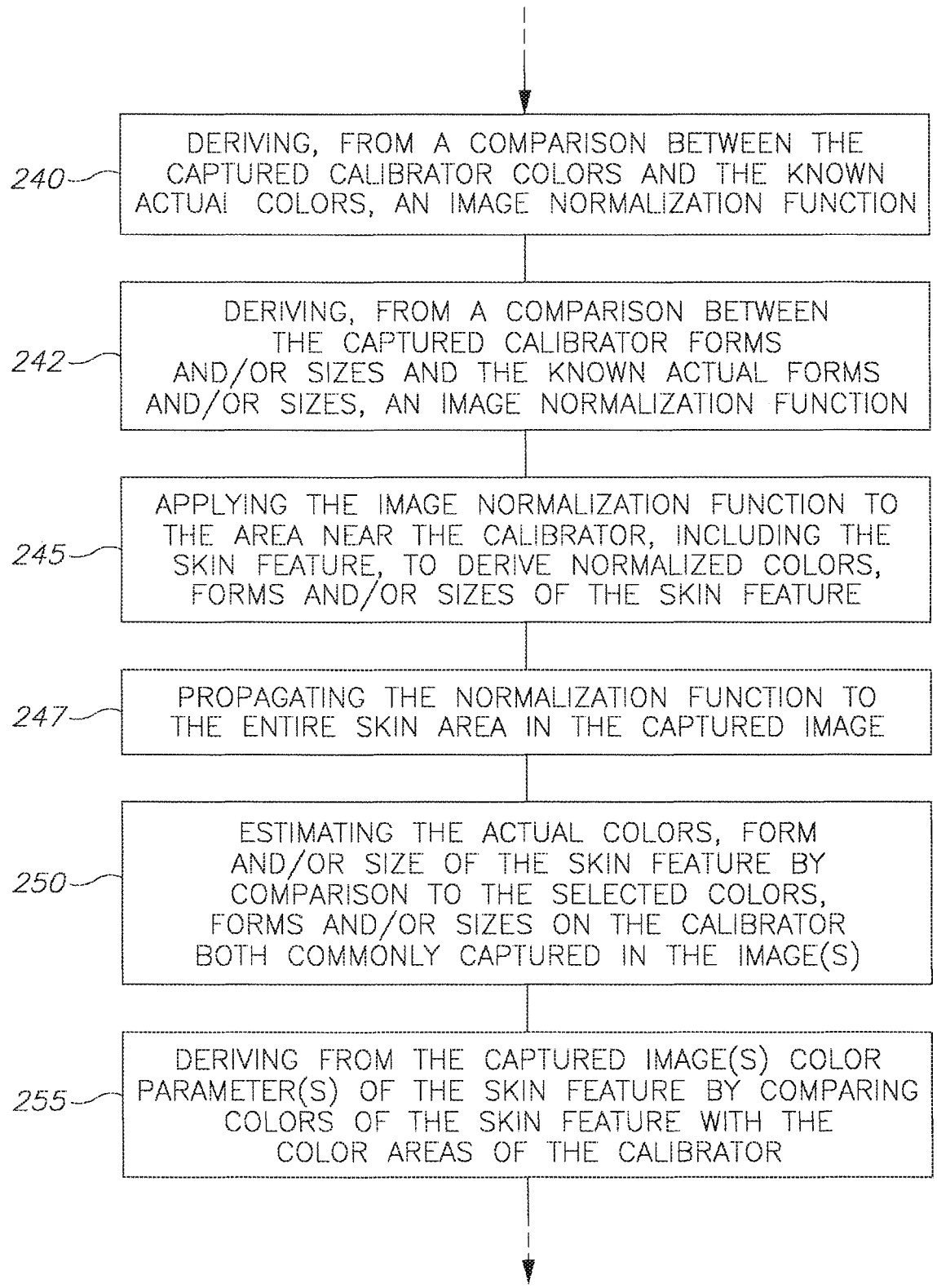
Figure 3 (cont. 1)

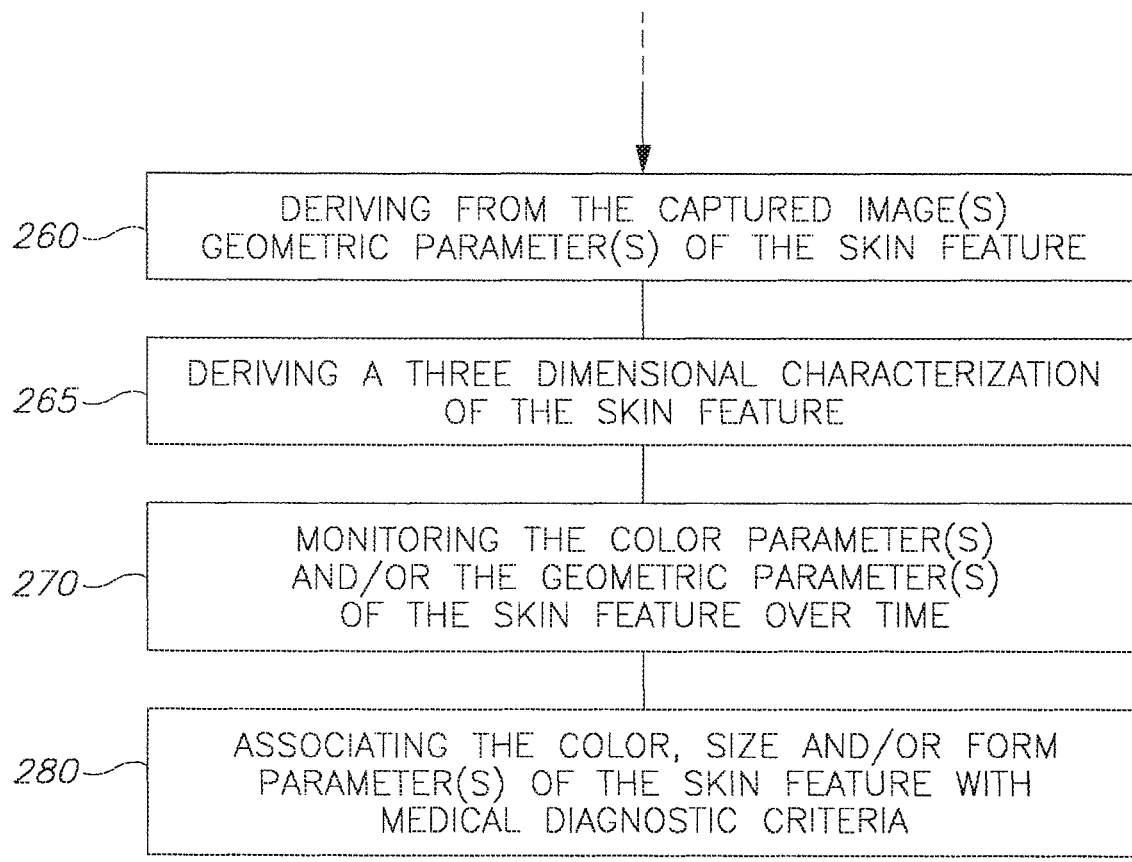
Figure 3 (cont. 2)

MEASURING AND MONITORING SKIN FEATURE COLORS, FORM AND SIZE

CROSS-REFERENCE TO RELATED APPLICATIONS

This application is a continuation of application Ser. No. 15/546,674, filed Jul. 27, 2017, which is a national phase application based on International Application No. PCT/IL2016/050069, filed Jan. 21, 2016, which claims the benefit of U.S. Provisional Application No. 62/108,097, filed Jan. 27, 2015, all which are incorporated herein by reference.

BACKGROUND OF THE INVENTION

1. Technical Field

The present invention relates to the field of image processing, and more particularly, to color measurements and skin diagnosis.

2. Discussion of Related Art

Identification and monitoring of changes in the skin are essential for prevention and timely treatment of skin irregularities associated with various medical conditions. Modern accessibility of imaging devices enables in principle image-based monitoring, yet technological barriers still inhibit reliable and effective use of image-based skin diagnosis.

SUMMARY OF THE INVENTION

One aspect of the present invention provides a kit comprising a calibrator having a plurality of selected colors, the calibrator attachable onto a skin area next to a skin feature, and an application configured to derive, from at least one captured image of the calibrator and the skin feature, an image normalization function from a comparison between captured calibrator colors and the selected calibrator colors, and to apply the image normalization function to the captured skin feature to yield normalized colors of the skin feature.

These, additional, and/or other aspects and/or advantages of the present invention are set forth in the detailed description which follows; possibly inferable from the detailed description; and/or learnable by practice of the present invention.

BRIEF DESCRIPTION OF THE DRAWINGS

For a better understanding of embodiments of the invention and to show how the same may be carried into effect, reference will now be made, purely by way of example, to the accompanying drawings in which like numerals designate corresponding elements or sections throughout.

In the accompanying drawings:

FIG. 1A is a high level schematic illustration of a calibrator next to a skin feature 90, according to some embodiments of the invention.

FIG. 1B schematically illustrates a representation of the color space as explained below, according to some embodiments of the invention.

FIG. 3 is a high level schematic flowchart illustrating a method, according to some embodiments of the invention.

DETAILED DESCRIPTION OF THE INVENTION

Figure 1C:
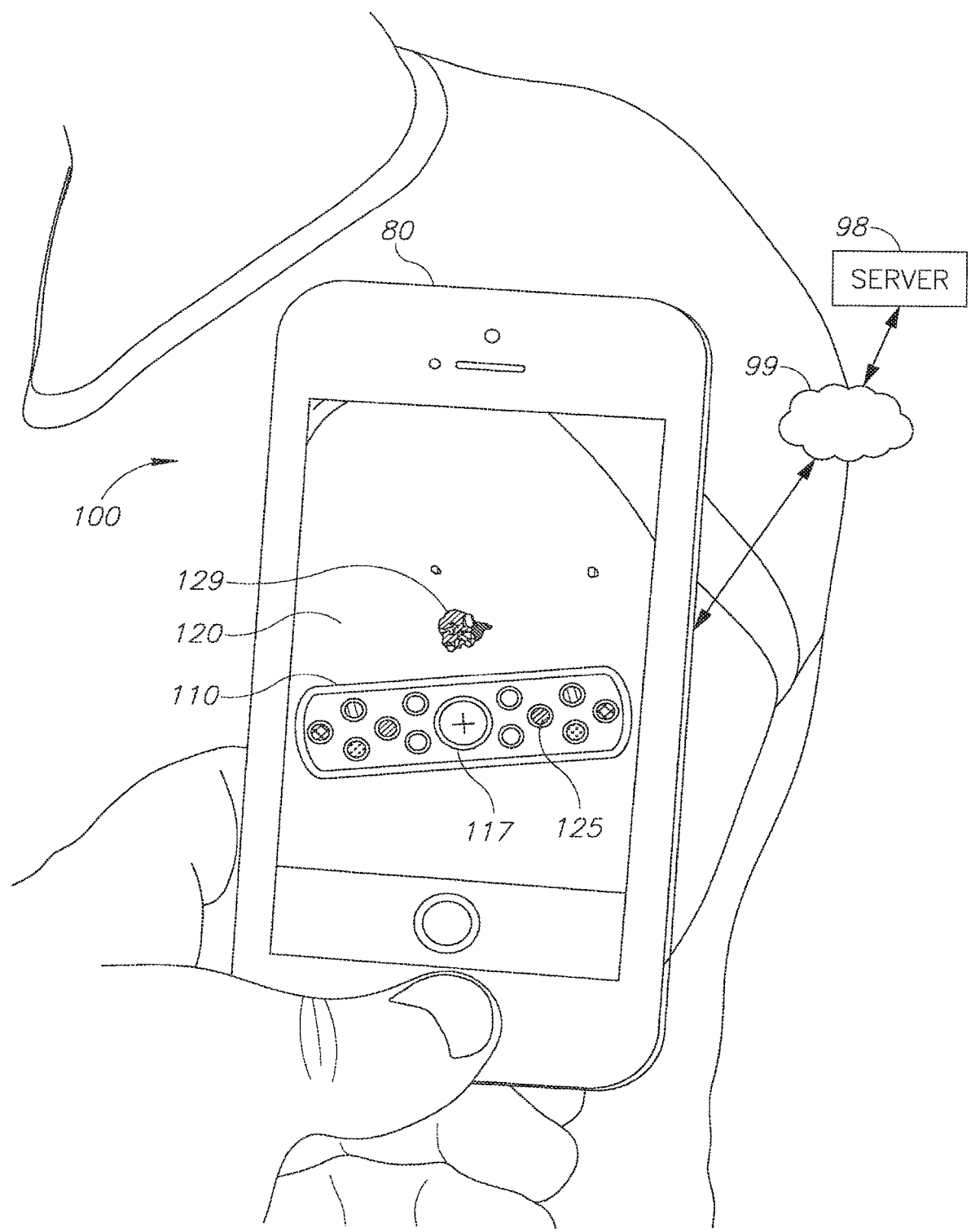
FIG. 1C is a high level schematic illustration of an image of the scene illustrated in FIG. 1A, according to some embodiments of the invention.

Prior to the detailed description being set forth, it may be helpful to set forth definitions of certain terms that will be used hereinafter.

The term "color" as used in this application refers to colors printed on a calibration template (calibrator) as well as to colors as captured in images of the printed colors and of skin features. It is noted that the term "color" as used in this application is referred to not subjectively but as having objectively measureable parameters such as spectral distribution or portions thereof and derived parameters such as color temperature, color space coordinates and any correlatives of color appearance (e.g., hue, tone, saturation etc.).

The term "medical condition" as used in this application refers to any dermatological state or phenomena of the skin, be it normal or abnormal. The term "skin feature" as used in this application refers to any skin characteristic or element, such as any skin lesions and various surface features.

With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

Before at least one embodiment of the invention is explained in detail, it is to be understood that the invention is not limited in its application to the details of construction and the arrangement of the components set forth in the following description or illustrated in the drawings. The invention is applicable to other embodiments or of being practiced or carried out in various ways. Also, it is to be understood that the phraseology and terminology employed herein is for the purpose of description and should not be regarded as limiting.

Kits, diagnostic systems and methods are provided, which measure the distribution of colors of skin features by comparison to calibrated colors which are co-imaged with the skin feature. The colors on the calibrating template (calibrator) are selected to represent the expected range of feature colors under various illumination and capturing conditions. The calibrator may also comprise features with different forms and size for calibrating geometric parameters of the skin features in the captured images. Measurements may be enhanced by monitoring over time changes in the distribution of colors, by measuring two and three dimensional geometrical parameters of the skin feature and by associating the data with medical diagnostic parameters. Thus, simple means for skin diagnosis and monitoring are provided which simplify and improve current dermatologic diagnostic procedures.

Figure 1D:
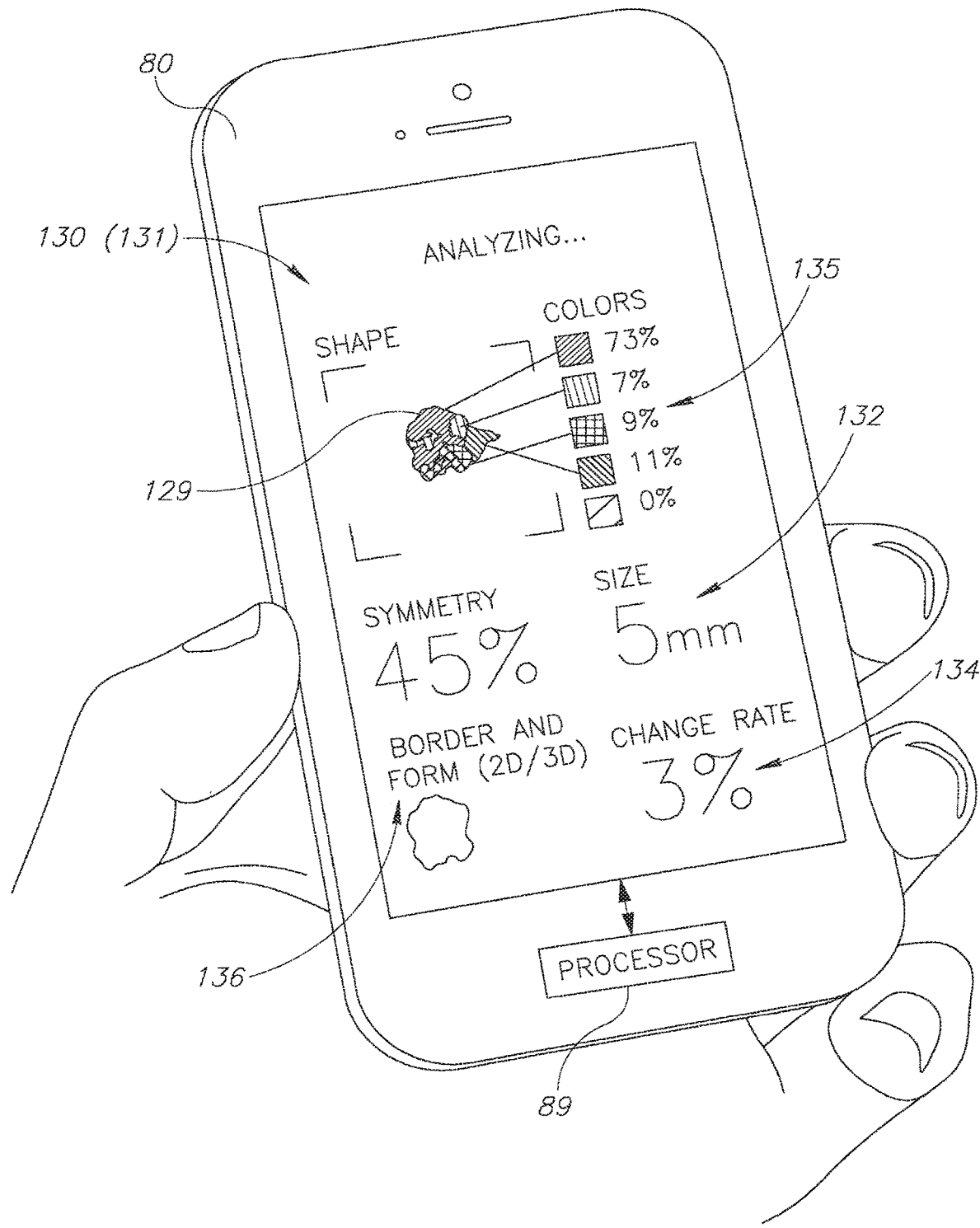
FIG. 1D is a high level schematic illustration of skin feature analysis results the images, according to some embodiments of the invention.

FIG. 1A is a high level schematic illustration of a calibrator 110 next to a skin feature 90, according to some embodiments of the invention. FIG. 1B schematically illustrates a representation of the color space as explained below, according to some embodiments of the invention. FIG. 1C is a high level schematic illustration of an image 120 of the scene illustrated in FIG. 1A, according to some embodiments of the invention. FIG. 1D is a high level schematic illustration of skin feature analysis results the images, according to some embodiments of the invention. Kits 100 may comprise a capturing device 80 (see below, e.g., a phone, a glass, etc.), one or more calibration aids 110 (also termed calibrator 110) and an application 130, which are disclosed in detail below. Calibration aid 110 is designed to have color and/or texture features that are derived from the colors/texture distributions of the plausible measured skin features 90.

Calibrator 110 comprises a plurality of selected colors 115 (e.g., 115A-E) and is attachable onto a skin area 91 next to skin feature 90. One or more images 120 of a skin feature 90 next to calibrator 110 are captured (FIG. 1C), and image processing methods are used to derive colors 90A-D of captured skin feature 129 (the numeral 129 denotes the image of skin feature 90) by comparison to captured colors 125 (the numeral 125 denotes the image of color areas 115 on calibrator 110). In certain embodiments, a kit 100 may comprise calibrator 110 and an application 130 configured to estimate, from at least one image 120 of skin feature 90 and of at least a part of calibrator 110, a distribution of colors 135 of imaged skin feature 129 by comparison to captured selected colors 125 on calibrator 110.

Calibrator 110 may further comprise one or more positioning marks 117 that may be used for image processing purposes and/or for positioning calibrator 110 accurately with respect to skin feature 90. Moreover, positioning mark(s) 117 may be used to estimate a size and/or a form of skin feature 90. In certain embodiments, positioning mark(s) 117 may be used, e.g., by an analysis module 101 (and/or application 130) to normalize captured image(s) 150 with respect to dimensions and forms, e.g., by analyzing size and/or form of positioning mark(s) 117 and/or calibrator 110 in image(s) 150, and furthermore to derive an analysis of size and/or form of skin feature 90 and possibly of other image features. For example, analysis module 101 and/or application 130 may compute the color constancy to tell whether two pixels have the same color in the real world regardless of illumination/camera parameters. Diagnosis may then be enhanced and diagnostic parameters may be derived from the normalized size and/or form data.

Normalization 150 (represented e.g., by a normalization function 150, see below) may be carried out with respect to various parameters, such as color and geometry, that characterize skin feature 90 in captured image 120. For example, normalization 150 with respect to color may be configured to remove illumination and camera pipeline effects from image 120 and particularly from imaged skin feature 129. More specifically, normalization 150 may be configured to reverse any of the tone mapping, color enhancement, white balance, sharpening and contrast enhancing of the camera. Normalization 150 may also be configured to simulate standard illumination conditions and reduce shading and specularity effects. Normalization 150 may be applied using one or more input images 120 and to one or more input images 120.

In certain embodiments, normalization 150 may be configured to provide geometric normalization of imaged skin feature 129, comprising e.g., projecting the skin feature onto a simulated perpendicular plane (for minimizing affine distortion) which can be done heuristically using a single image (based on the appearance of the calibrator or shape from shading), or computationally using two or more images. Additionally, system 102 may provide two dimensional measurements of the skin features, specifically size and shape characteristics (symmetry, boundary length etc.).

In certain embodiments, calibrator 110 may have different forms, adapted to the medical condition, form or expected form and characteristics of skin feature(s) 90 and adapted to the capturing conditions (e.g., to capturing geometry). For example, calibrator 110 may be round, elongated, curved, have one or more holes to accommodate skin feature(s) 90 etc. One or more colors 115, e.g., color 115A, may be used for calibrating illumination and capturing conditions rather than or in addition to relating to expected colors in skin feature 90.

Colors 115 may be selected with respect to specific medical conditions and may differ between different, respectively designated kits 100. For example, calibrators 110 for melanomas may comprise shades of brown and red while calibrators 110 from scars may comprise shades of red and yellow.

Kit 100 may comprise calibrator 110 having a plurality of selected colors 115 which is attachable onto skin area 91 next to skin feature 90, and application 130 configured to derive, from at least one captured image 120 of calibrator 110 and skin feature 90, an image normalization function from a comparison between captured calibrator colors 125 and selected calibrator colors 115, and to apply the image normalization function to captured skin feature 129 to yield normalized colors of skin feature 90.

FIG. 1B schematically illustrates a generalized, abstract color space defined by arbitrary measures $X_1$, $X_2$, and a region in the color space that holds all possible colors 90A-Z which are expected at a given medical situation relating to the skin feature 90 (e.g., possible colors of specified skin lesions such as nevi, melanomas, scars, etc.). Specific colors 115A-E (in a non-limiting example) may be selected to span the color region defined by possible colors 90A-Z in order to optimize detection efficiency and maximized the data which is derivable from the captured images. In certain embodiments, one or more of colors 115 may be used for calibration rather than for spanning the color region.

Application 130 may operate at an image capturing device 80 such as a smartphone (e.g., run by a processor 89, FIG. 1D). In certain embodiments, image 120 may be captured by a communication device 80 an at least a part of application 130 may run remotely, e.g., on a server 98 over a communication link 99, such as a cloud server (FIG. 1C). Application 130 (represented in FIG. 1D by an output display 131 which may be configured as a graphical user interface as well, application 130 may run at least partly remotely) may be configured to analyze skin feature image 129 with respect to various parameters such as distribution of colors 135, one or more geometric parameter 136 (e.g., form, border, symmetry, two or three dimensional form), dimensions 132 (e.g., size or height) etc. Calibrator 110 may comprise a plurality of geometric parameter designations which are used to derive geometric parameter(s) 136, 132, e.g., form and size of skin feature 90. The geometric parameter designations may comprise features with differing sizes or forms such as various positioning marks 117, color areas holding colors 115 or any other geometrical features.

Application 130 may be configured to derive any of the above mentioned parameters and their combinations. Application 130 may be further configured to track distribution of colors 135 and/or other skin feature parameters over time, using multiple, periodically captured images 120, and present temporal parameters 132, such as a rate of change of any of the skin feature parameters. In certain embodiments, application 130 may be further configured to identify a three dimensional structure of skin feature 90 using multiple captured images 120, e.g., taken from different directions and at different angles and/or illumination conditions. Either or both two-dimensional and three-dimensional geometrical parameter and structural information may be tracked over time.

Tracking skin feature parameters over time may be carried out by repeatedly capturing the same skin feature over. For example a scar tissue or a rush as skin feature 90 may be monitored daily for tracking healing progress, or a suspected skin feature 90 may be captured weekly or even monthly for monitoring for potentially cancerous features. When having input from multiple occasions an additional optimization step may be added for verifying the normalization is consistent across the entire time frame. Normalization 150 may further comprise adapting the normalization function and procedures to take into account capturing over time at varying conditions, including varying skin appearance.

Figure 2A:
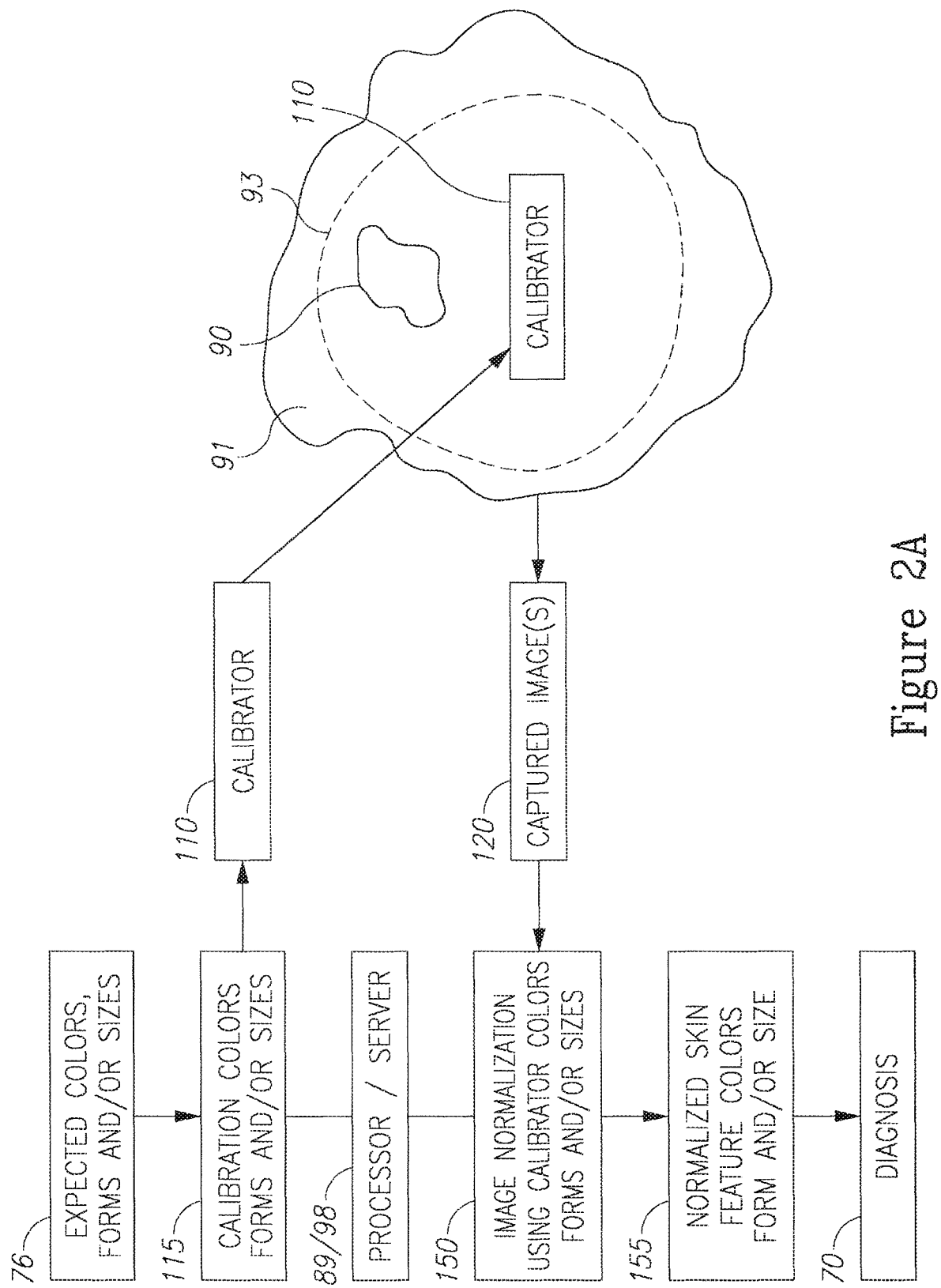
FIG. 2A is a high level schematic functional illustration, according to some embodiments of the invention.

FIG. 2A is a high level schematic functional illustration, according to some embodiments of the invention. From a set or a range of expected colors 76 (e.g., 90A-Z), a set of calibration colors 115 may be selected to optimize a normalization of images of skin areas 91 under expected illumination and capturing conditions. In certain embodiments, calibration colors 115 may comprise additional colors which are beyond the expected range of colors, to enhance calibration or to separate the effects of illumination conditions and capturing conditions (e.g., the effects of camera sensors). For example, some of colors 115 may be used to characterize the illumination conditions irrespectively of the specific skin area 91 and expected colors 76. Calibrator 110 with colors 115 may then be set or attached within skin area 91 next to skin feature 90. In captured image(s) 120, captured colors 135 may be compared to calibration colors 115 to derive a normalization function (e.g., pixel-wise), which may then be applied (e.g., pixel-wise) to captured vicinity 93 of calibrator 110 that includes at least a part of imaged skin feature 129. The normalization function may be applied (150) to different vicinity extents 93, depending on the uniformity of illumination and capturing conditions (e.g., in a controlled environment, vicinity 93 may be larger than uncontrolled environments, or the extent of variation of illumination and capturing conditions in images 120 may be estimated). From normalization 150, normalized skin and skin features may be derived 155 to correspond with actual skin and skin feature colors 90 and be used for diagnosis 70. In certain embodiments, skin color may be used to further process skin feature colors, e.g., remove by processing effects applied to the whole of skin area 91 such as tanning or skin treatment (e.g., applied makeup or other skin products). Color selection and optimization and/or image normalization and diagnosis may be carried out at least partially by processor 89 and/or server 98.

In certain embodiments, set(s) of calibration forms and/or sizes 115 may be selected from respective set(s) or range(s) of expected forms and sizes of skin features 76, to optimize a normalization of images of skin areas 91 under expected illumination and capturing conditions. For example, different forms may be printed on calibrator 110, or color areas 115 may be printed with different forms and/or sizes. In captured image(s) 120, captured forms and/or sizes may be compared to calibration forms and/or sizes to derive a normalization function (e.g., pixel-wise), which may then be applied (e.g., pixel-wise) to captured vicinity 93 of calibrator 110 that includes at least a part of imaged skin feature 129. The normalization function may be applied (150) to different vicinity extents 93, depending on the uniformity of illumination and capturing conditions (e.g., in a controlled environment, vicinity 93 may be larger than uncontrolled environments, or the extent of variation of illumination and capturing conditions in images 120 may be estimated). From normalization 150, normalized skin and skin features may be derived 155 to correspond with actual skin and skin feature form and/or size, and be used for diagnosis 70. Selection, optimization and/or image normalization and diagnosis with respect to form and/or size of skin feature 90 may be carried out at least partially by processor 89 and/or server 98.

Figure 2B:
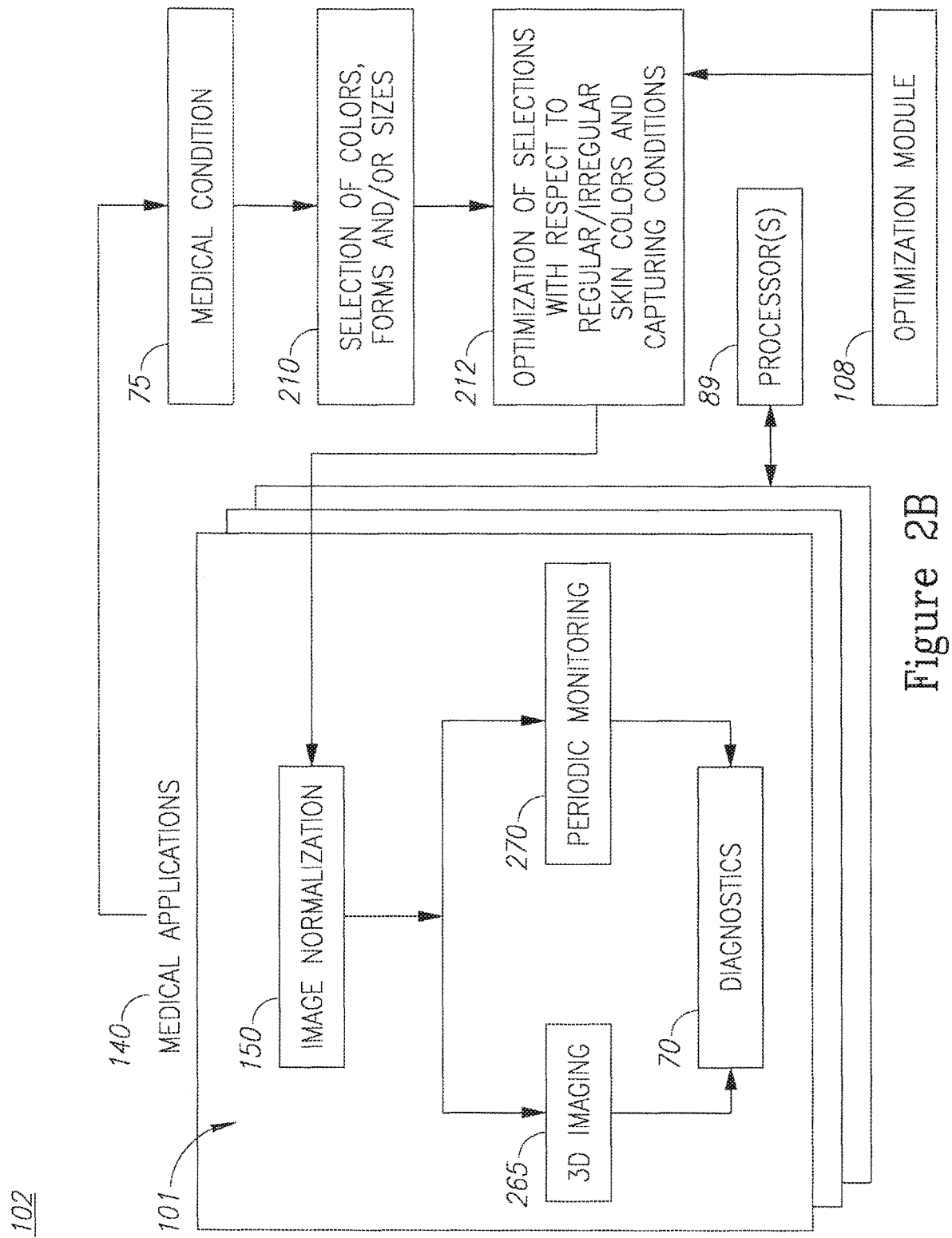
FIG. 2B is a high level schematic block diagram of a diagnostic system, according to some embodiments of the invention.

FIG. 2B is a high level schematic block diagram of a diagnostic system 102, according to some embodiments of the invention. Diagnostic system 102 may comprise one or more kit 100 and may be used to develop kits 100 with respect to specified medical conditions 75. Given a medical application 140 (e.g., skin lesions such as nevi, melanomas, scars, surface changes, scales, bites, ulcers etc.), colors 115 and/or forms and/or sizes may be selected 210 (e.g., by a selection module 210) according to medical diagnosis parameters. Colors 115 and/or forms and/or sizes may further be optimized 212 (e.g., by an optimization module 108) with respect to regular and irregular skin colors, as well as with respect to varying illumination and capturing conditions. Optimization module 108 may be configured to optimize a color selection and/or selection of forms and/or of sizes with respect to any of medical condition 75, a range of illumination parameters and a variety of capturing conditions. Specifically, optimization module 108 may be further configured to optimize the color selection by spanning a color space (e.g., 90A-Z in non-limiting FIG. 1B) defined by specified ranges of illumination parameters and capturing conditions.

For example, colors may be selected to be comparable to expected colors of skin feature 90 under common illumination conditions such as outdoors illumination, indoors illumination by typical illumination sources or illumination by typical capturing device illumination characteristics; and under common capturing conditions such as common capturing device sensor types and capturing scenarios. Application 130 may be configured to generate an alert when illumination conditions or capturing conditions are inappropriate for color detection and suggest modification thereof to enter a performance envelop of application 130. Colors 115 may be selected to widen the performance envelop. In certain embodiments, varieties of calibrator 110 may be used under different illumination and capturing conditions, e.g., calibrators 110 with larger or smaller number of colored areas and/or colors 115 may be used under different conditions.

Diagnostic system 102 may comprise calibrator(s) 110 selected according to medical condition 75, imaging device 80 configured to capture at least one image 120 of at least part of skin feature 90 and at least part of calibrator(s) 110, and an analysis module 101 (comprising e.g., application 130) configured to derive, from at least one captured image 120 of calibrator 110 and skin feature 90, an image normalization function from a comparison between captured calibrator colors 135 and selected calibrator colors 115, and to apply the image normalization function to captured skin feature 129 to yield normalized colors of skin feature 90. In certain embodiments, analysis module 101 (comprising e.g., application 130) may be configured to derive, by comparison of captured colors between the calibrator (125) and the skin feature (129), a medical diagnostic indication relating to medical condition 75.

Analysis module 101 (and/or application 130) may be configured to normalize the captured image(s) 150 (e.g., by analyzing calibration colors 115A or by measuring reference regions of calibration template such as positioning mark 117) and derive the distribution of colors and possibly geometric parameters of skin feature 90 to yield respective diagnostic parameters or a diagnosis 70. In certain embodiments, analysis module 101 may be further configured to track the medical diagnostic indication over time 270, using comparisons from multiple, periodically captured images. In certain embodiments, analysis module 101 may be further configured to enhance the derivation of the medical diagnostic indication by three dimensional structural data 265 relating to skin feature 90, derived from multiple images of skin feature 90.

In certain embodiments, the three dimensional geometry of skin feature 90 may be computed using two or more calibrated images 120. Calibration may be carried out in system 102, by application 130 and/or by analysis module 101, e.g., offline for each camera type and be verified or recalculated online based on the calibration patches. Crude geometry may be computed using matched feature points across several input images. Refined geometry may be computed using stereo block matching.

In certain embodiments, calibrator 110 may further comprise a plurality of geometric parameter designations comprising features with differing sizes or forms. Analysis module 101 may be further configured to derive from image(s) 120 the image normalization function from a comparison between captured geometric parameter designations and the calibrator geometric parameter designations, and to apply the image normalization function to the captured skin feature to yield normalized geometric parameters of the skin feature. For example, form and size of skin feature 90 may be thus normalized with respect to capturing conditions such as distance and angle of capturing. Either or both two-dimensional and three-dimensional geometrical parameter and structural information may be tracked over time.

In certain embodiments, diagnostic system 102 and kit 100 may be designed to operate in a single use mode and/or in a repeated use mode, the latter providing continued monitoring of the measured features. Any of color, texture, two dimensional (e.g., form, size) or three dimensional parameters of skin feature 90 may be measured in wither single use mode or repeated use mode. Color, texture and two dimensional parameters may be applied by image normalization with respect to the corresponding parameter and three dimensional parameters may be applied using a three dimensional reconstruction. Diagnostic system 102 and kit 100 may comprise a diagnostic layer with diagnostics relating to any of these parameters and operation modes.

FIG. 3 is a high level schematic flowchart illustrating a method 200, according to some embodiments of the invention. Respective stages may be at least partly carried out by a computer processor such as processor 89 or a processor on server 98, and/or implemented by application 130 and/or analysis module 101. Method 200 comprises at least an imaging processing part, a medical diagnosis part and a kit configuration part, which may be carried out independently or in combination.

Certain embodiments of method 200 comprise selecting a plurality of colors and/or forms and/or sizes according to expected colors and/or forms and/or sizes in a skin feature, a specified set of illumination conditions and a specified set of capturing parameters (stage 210), preparing a calibrator having the selected colors and/or forms and/or sizes to be attachable onto a skin area next to a skin feature (stage 220), and estimating a distribution of the actual colors and/or forms and/or sizes of a skin feature by comparison to the selected colors and/or forms and/or sizes on the calibrator commonly captured on at least one image (stage 250).

In certain embodiments, method 200 may comprise deriving, from a comparison between the captured calibrator colors (and/or forms and/or sizes) and the known actual colors (and/or forms and/or sizes), an image normalization function (stages 240, 242) and applying the image normalization function to the area near the calibrator, including the skin feature, to derive normalized colors and/or forms and/or sizes of the skin feature (stage 245). The normalization function may be propagated to the entire skin area in the captured image (stage 247).

In certain embodiments, method 200 may further comprise capturing at least one image of the skin feature and at least a part of the calibrator (stage 230). Method 200 may further comprise optimizing the color selection with respect to varying illumination and capturing conditions (stage 212).

Certain embodiments of method 200 comprise attaching a calibrator comprising a plurality of color areas and/or areas with different forms and/or sizes onto a skin area next to a skin feature (stage 225), capturing at least one image of the skin area, which includes both the skin feature and at least a part of the calibrator (stage 230), and deriving from the at least one captured image at least one color parameter of the skin feature by comparing colors of the skin feature with the color areas of the calibrator (stage 255) as well as form and size parameters. Method 200 may further comprise selecting the color areas to span a color space defined by a medical application (stage 215).

In certain embodiments, method 200 may further comprise associating the at least one color, form and/or size parameter of the skin feature with medical diagnostic criteria (stage 280).

Embodiments of method 200 may further comprise deriving from the at least one captured image at least one geometric parameter of the skin feature (stage 260). Embodiments of method 200 may further comprise capturing a plurality of images of the skin feature (stage 232) and deriving a three dimensional characterization of the skin feature therefrom (stage 265). Embodiments of method 200 may further comprise monitoring the at least one color parameter of the skin feature over time in periodically captured images (stage 270).

Certain embodiments comprise a computer program product comprising a computer readable storage medium having computer readable program embodied therewith, the computer readable program configured to estimate, in at least one captured image, a distribution of colors of a skin feature in the at least one image by comparison thereof to selected colors on a calibrator which is also captured in the at least one image. Certain embodiments comprise a computer program product comprising a computer readable storage medium having computer readable program embodied therewith, the computer readable program configured to derive, from at least one captured image of a calibrator having selected colors and a skin feature, an image normalization function from a comparison between captured calibrator colors and the selected calibrator colors, and to apply the image normalization function to the captured skin feature to yield normalized colors of the skin feature. Additional computer readable program may be configured to carry out any of the data processing stages disclosed above.

In the above description, an embodiment is an example or implementation of the invention. The various appearances of "one embodiment", "an embodiment", "certain embodiments" or "some embodiments" do not necessarily all refer to the same embodiments.

Although various features of the invention may be described in the context of a single embodiment, the features may also be provided separately or in any suitable combination. Conversely, although the invention may be described herein in the context of separate embodiments for clarity, the invention may also be implemented in a single embodiment.

Certain embodiments of the invention may include features from different embodiments disclosed above, and certain embodiments may incorporate elements from other embodiments disclosed above. The disclosure of elements of the invention in the context of a specific embodiment is not to be taken as limiting their used in the specific embodiment alone.

Furthermore, it is to be understood that the invention can be carried out or practiced in various ways and that the invention can be implemented in certain embodiments other than the ones outlined in the description above.

The invention is not limited to those diagrams or to the corresponding descriptions. For example, flow need not move through each illustrated box or state, or in exactly the same order as illustrated and described.

Meanings of technical and scientific terms used herein are to be commonly understood as by one of ordinary skill in the art to which the invention belongs, unless otherwise defined.

While the invention has been described with respect to a limited number of embodiments, these should not be construed as limitations on the scope of the invention, but rather as exemplifications of some of the preferred embodiments. Other possible variations, modifications, and applications are also within the scope of the invention. Accordingly, the scope of the invention should not be limited by what has thus far been described, but by the appended claims and their legal equivalents.

The invention claimed is:

1. A non-transitory computer readable storage medium storing instructions that, when executed by a processor, cause the processor to perform a method for three-dimensional image skin diagnosis, the method comprising:
   receiving a group of images of a skin feature next to a calibrator having a plurality of colored areas thereon, wherein the skin feature has multiple segments of differing colors;
   identifying, using the group of images, a three-dimensional structure of the skin feature;
   identifying, using the plurality of colored areas of the calibrator, the differing colors of the multiple segments of the skin feature, wherein the identification includes determining actual colors of the multiple segments of the skin feature by comparison of the colors of the multiple segments of the skin feature to the plurality of colored areas of the calibrator commonly captured on at least one image; and
   based on the identified three-dimensional structure of the skin feature and the differing colors of the multiple segments of the skin feature, determining an indication of a medical condition associated with the skin feature.

2. The non-transitory computer readable storage medium of claim 1, wherein identifying the three-dimensional structure of the skin feature includes determining at least one three-dimensional geometrical parameter of the skin feature.

3. The non-transitory computer readable storage medium of claim 1, wherein determining the indication of the medical condition is based on a rate of change of at least one skin feature parameter selected from a group including: a distribution of colors, a three-dimensional geometrical parameter, and dimensions of at least one segment of the skin feature.

4. The non-transitory computer readable storage medium of claim 3, wherein the method further comprises:
   tracking the medical condition over time using comparisons from multiple groups of images received periodically.

5. The non-transitory computer readable storage medium of claim 1, wherein the method further comprises:
   monitoring temporal changes of at least one skin feature parameter selected from a group including: a distribution of colors, a three-dimensional geometrical parameter, and dimensions of at least one segment of the skin feature to track a healing progress of a skin feature.

6. The non-transitory computer readable storage medium of claim 1, wherein the plurality of colored areas are associated with an expected range of colors of the skin feature under various illumination and capturing conditions.

7. The non-transitory computer readable storage medium of claim 1, wherein the method further comprises:
   determining distribution of colors in the three-dimensional structure of the skin feature; and
   determining the indication of the medical condition based on the distribution of colors in the three-dimensional structure.

8. The non-transitory computer readable storage medium of claim 1, wherein the method further comprises:
   determining a height of the three-dimensional structure of the skin feature; and
   determining the indication of the medical condition based on the height of the three-dimensional structure.

9. A method for three-dimensional image skin diagnosis, the method comprising:
   receiving a group of images of a skin feature next to a calibrator having a plurality of colored areas thereon, wherein the skin feature has multiple segments of differing colors;
   identifying, using the group of images, a three-dimensional structure of the skin feature;
   identifying, using the plurality of colored areas of the calibrator, the differing colors of the multiple segments of the skin feature, wherein the identification includes determining actual colors of the multiple segments of the skin feature by comparison of the colors of the multiple segments of the skin feature to the plurality of colored areas of the calibrator commonly captured on at least one image; and
   based on the identified three-dimensional structure of the skin feature and the differing colors of the multiple segments of the skin feature, determining an indication of a medical condition associated with the skin feature.

10. The method of claim 9, wherein the plurality of colored areas on the calibrator have different sizes.

11. The method of claim 9, wherein the calibrator includes a first set of colors expected to be found in the skin feature.

12. The method of claim 11, wherein the calibrator includes a second set of colors different from the first set for calibrating illumination conditions.

13. The method of claim 11, further comprising:
determining a skin color of a patient; and
considering the skin color when identify the differing colors of the multiple segments of the skin feature.

14. The method of claim 11, further comprising:
identifying at least one illumination condition associated with the group of images; and
reducing the effect of the at least one illumination condition on the differing colors of the multiple segments of the skin feature.

15. The method of claim 14, further comprising:
generating an alert when at least one illumination condition is inappropriate for accurate color detection; and
suggesting a modification to the identified at least one illumination condition.

16. The method of claim 9, wherein the calibrator includes one or more holes to accommodate the skin feature.

17. The method of claim 9, further comprising:
identifying at least one capturing condition associated with the group of images; and
reducing the effect of the at least one capturing condition on the differing colors of the multiple segments of the skin feature.

18. The method of claim 9, further comprising:
generating an alert when at least one capturing condition is inappropriate for accurate color detection; and
suggesting a modification to the identified at least one capturing condition.

19. A system for three-dimensional image skin diagnosis, the system comprising:
at least one processing device configured to;
receive a group of images of a skin feature next to a calibrator having a plurality of colored areas thereon, wherein the skin feature has multiple segments of differing colors;
identify, using the group of images, a three-dimensional structure of the skin feature;
identify, using the plurality of colored areas of the calibrator, the differing colors of the multiple segments of the skin feature, wherein the identification includes determining actual colors of the multiple segments of the skin feature by comparison of the colors of the multiple segments of the skin feature to the plurality of colored areas of the calibrator commonly captured on at least one image; and
based on the identified three-dimensional structure of the skin feature and the differing colors of the multiple segments of the skin feature, determine an indication of a medical condition associated with the skin feature.

* * * * *